United States Patent

Paul et al.

[11] Patent Number: 6,002,045
[45] Date of Patent: Dec. 14, 1999

[54] RACEMISATION OF AMINES

[75] Inventors: Jane Marie Paul, Cambridge; Gerard Andrew Potter, Leicester, both of United Kingdom

[73] Assignee: Chirotech Technology Limited, United Kingdom

[21] Appl. No.: 09/077,433

[22] PCT Filed: Dec. 13, 1996

[86] PCT No.: PCT/GB96/03100

§ 371 Date: Jun. 12, 1998

§ 102(e) Date: Jun. 12, 1998

[87] PCT Pub. No.: WO97/21662

PCT Pub. Date: Jun. 19, 1997

[30] Foreign Application Priority Data

Dec. 14, 1995 [GB] United Kingdom .................... 9525496

[51] Int. Cl.⁶ .................................................. C07C 204/00

[52] U.S. Cl. .................................................. 564/302
[58] Field of Search .............................................. 564/302

[56] References Cited

U.S. PATENT DOCUMENTS 5,200,561   4/1993   Konya et al. ........................... 564/373

*Primary Examiner*—Samuel Barts
*Attorney, Agent, or Firm*—Saliwanchik, Lloyd & Saliwanchik

[57] ABSTRACT

A process for racemising an optically-enriched chiral amine of the formula: $R^1$—$CH(NR^3R^4)$—$R^2$, wherein $R^1$ is aromatic or unsaturated alkyl; $R^2$ is aromatic or alkyl; and $R^3$ and $R^4$ are independently selected from hydrogen, alkyl and aryl; and wherein any combination(s) of two of the R groups may form a ring; comprises treatment of the optically-enriched amine with a metal hydroxide in an aprotic polar solvent.

9 Claims, No Drawings

RACEMISATION OF AMINES

This application is a 371 of PCT/GB96/03100 filed Dec. 13, 1996.

FIELD OF THE INVENTION

The invention relates to a process for the racemisation of optically-active akmines, e.g. 1-arylalkylamines.

BACKGROUND OF THE INVENTION

Optically pure amines are useful as industrial chemicals and as intermediates for agrochemicals and pharmaceuticals. They are frequently obtained conveniently by chemical resolution through salt formation at the amine function. Alternatively, enzymatic resolution of the racemate can be applied. Either way, the method separates the two enantiomers, only one of which is generally desired. In order to obtain an economic overall process, it then becomes desirable to effect racemisation of the undesired enantiomer, so that it can be recycled back into the resolution.

DE-A-2851039 discloses the racemisation of 1-arylalkylamines using a metal catalyst, for example hydrogen and Raney cobalt. JP-A-1471389 discloses the use of a catalyst comprising alkali metals and polyaromatic hydrocarbons. DE-A-2442854 discloses the use of a catalyst prepared from sodium or potassium or their hydroxides on alumina. Racemisation of 1-arylalkylamines by treatment with alkali metal or alkaline earth metal alkoxides in dimethyl sulfoxide at 0–200° C. is also known; see U.S. Pat. No. 5,183,939.

Limitations of the available methods are the costs of the catalyst/reagents for a recycling process, and the sometimes vigorous conditions, leading to the formation of side products.

SUMMARY OF THE INVENTION

The present invention is based on the surprising discovery that optically-active amines $R^1.CH(NR^3R^4).R^2$ may be racemised simply and cleanly by treatment with a metal hydroxide in an aprotic polar solvent such as dimethyl sulfoxide. In this amine, $R^1$ represents an aromatic, alkenyl or alkynyl residue, $R^3$ and $R^4$ are independently hydrogen or an alkyl or aryl residue, and $R^2$ is an alkyl residue that may optionally have additional substitution such as hydroxyl group. The groups on the nitrogen, i.e. $R^3$ and $R^4$, optionally may form one or more rings with the groups $R^1$ and/or $R^2$.

DESCRIPTION OF THE INVENTION

Metal hydroxides used in the novel process are of alkali metals or alkaline earth metals, and preferably sodium or potassium hydroxide.

In general, relative to 1 mol of substrate amine, between 0.01 and 5 mol, but preferably not more than 0.2 mol of hydroxide in between 1 and 20 mol of dimethyl sulfoxide, but preferably less than 10 mol, are employed at temperatures between 40–180° C., but preferably at less than 100° C., with reaction times in the range 1–48 h. After racemisation has occurred, the amine may be isolated using normal work-up procedures.

This procedure is advantageous over the prior art since metal hydroxides, particularly potassium hydroxide and sodium hydroxide, are cheaper, are more widely available, and/or more easily stored than the catalysts/reagents described in the prior art.

The following Example illustrates the invention.

EXAMPLE

Solid, powdered potassium hydroxide (4.6 mg, $8.2 \times 10^{-5}$ mol) and (R)-1-phenylethylamine (98% ee) (1.00 g, $8.25 \times 10^{-3}$ mol) are mixed with dimethyl sulfoxide (5 ml, 0.07 mol), and the mixture is heated to 80°C. and kept at this temperature for 16 h. The mixture is then cooled and diluted with water (5 ml), and the amine is extracted into ether (2×10 ml). The combined organic layers are washed with brine, dried over $MgSO_4$, filtered and concentrated to give 0.85 g (85%) of substantially racemic 1-phenylethylamine; purity >96% by $^1HNMR$, ratio (S):(R) recovered by HPLC with chiral column as 1:1.

We claim:

1. A process for racemising an optically-enriched chiral amine of the formula $$R^1\text{—}CH(NR^3R^4)\text{—}R^2$$

wherein $R^1$ is aromatic or unsaturated alkyl; $R^2$ is aromatic or alkyl; and $R^3$ and $R^4$ are independently selected from the group consisting of hydrogen, alkyl and aryl; and wherein any combination(s) of two of the R groups may form a ring; wherein said process comprises treatment of the optically-enriched amine with a metal hydroxide in an aprotic polar solvent.

2. The process according to claim 1, where the metal hydroxide is sodium or potassium hydroxide.

3. The process according to claim 2, where the metal hydroxide is potassium hydroxide.

4. The process according to claim 1, where the metal hydroxide is powdered, and said powdered metal hydroxide and said amine are mixed in said solvent.

5. The process according to claim 1, where $R^1$ is aromatic.

6. The process according to claim 1, where the amine is a primary amine.

7. The process according to claim 1, where each R group has no more than 10 C atoms.

8. The process according to claim 6, where the amine is 1-phenylethylamine.

9. The process according to claim 6, where the amine is $R^1.CH(NH_2).R^2$.

* * * * *

UNITED STATES PATENT AND TRADEMARK OFFICE
CERTIFICATE OF CORRECTION

PATENT NO. : 6,002,045
DATED : December 14, 1999
INVENTOR(S) : Jane Marie Paul, Gerard Andrew Potter It is certified that error appears in the above-identified patent and that said Letters Patent is hereby corrected as shown below:

Column 2,
Line 46: "where $R^1$ is aromatic." should read -- where the solvent is dimethyl sulfoxide --.

Signed and Sealed this

Thirty-first Day of July, 2001

Attest:

Attesting Officer

NICHOLAS P. GODICI
*Acting Director of the United States Patent and Trademark Office*